United States Patent
Nakamura et al.

(10) Patent No.: US 10,328,665 B2
(45) Date of Patent: Jun. 25, 2019

(54) NONWOVEN FABRIC, AND DUST COLLECTING FILTER, MEDIUM OF MICROORGANISM OR BIOLOGICAL TISSUE, AND COSMETIC ARTICLE, EACH HAVING THE SAME

(71) Applicant: Panasonic Intellectual Property Management Co., Ltd., Osaka (JP)

(72) Inventors: Taichi Nakamura, Osaka (JP); Takayoshi Yamaguchi, Osaka (JP); Hiroto Sumida, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 182 days.

(21) Appl. No.: 15/372,794

(22) Filed: Dec. 8, 2016

(65) Prior Publication Data

US 2017/0210088 A1    Jul. 27, 2017

(30) Foreign Application Priority Data

Jan. 27, 2016  (JP) .................... 2016-012908

(51) Int. Cl.
| | | |
|---|---|---|
| *B32B 3/10* | (2006.01) | |
| *B32B 5/02* | (2006.01) | |
| *B01D 39/16* | (2006.01) | |
| *C12N 5/00* | (2006.01) | |

(52) U.S. Cl.
CPC ............ *B32B 5/022* (2013.01); *B01D 39/163* (2013.01); *C12N 5/0068* (2013.01); *B01D 2239/065* (2013.01); *B01D 2239/0618* (2013.01); *B01D 2239/0622* (2013.01); *B01D 2239/0636* (2013.01); *B01D 2239/10* (2013.01); *B01D 2239/1233* (2013.01); *B32B 2305/026* (2013.01)

(58) Field of Classification Search
None
See application file for complete search history.

(56) References Cited

U.S. PATENT DOCUMENTS

| | | | | |
|---|---|---|---|---|
| 4,265,954 A | * | 5/1981 | Romanek ............... | B29C 65/02 156/181 |
| 2009/0324905 A1 | * | 12/2009 | Welch ............... | A61F 13/15593 428/198 |
| 2010/0269464 A1 | * | 10/2010 | Mori .................. | B01D 39/1692 55/486 |

(Continued)

FOREIGN PATENT DOCUMENTS

| | | |
|---|---|---|
| JP | 2007-224466 A | 9/2007 |
| JP | 2012-200152 A | 10/2012 |

(Continued)

*Primary Examiner* — Christopher M Polley
(74) *Attorney, Agent, or Firm* — Pearne & Gordon LLP (57) ABSTRACT

A nonwoven fabric contains a plurality of fibers having average fiber diameter $D_{ave}$ in a range from 10 nm to 3 μm, inclusive. The nonwoven fabric has a plurality of fusion portions among the plurality of fibers. The nonwoven fabric has a first principal surface and a second principal surface on an opposite side to the first principal surface. Average number Nh of the fusion portions observed per 500 μm² on the first principal surface is six or more.

6 Claims, 2 Drawing Sheets

(56) References Cited

U.S. PATENT DOCUMENTS

| | | | | |
|---|---|---|---|---|
| 2012/0180800 A1* | 7/2012 | Shibata | ............... | A41D 13/113 |
| | | | | 128/863 |
| 2012/0249629 A1 | 10/2012 | Yabuki | | |
| 2014/0223872 A1* | 8/2014 | Bao | ....................... | B01D 39/16 |
| | | | | 55/486 |
| 2016/0051917 A1* | 2/2016 | Seeberger | ............ | D01D 5/0985 |
| | | | | 55/521 |
| 2016/0367922 A1* | 12/2016 | Kamiyama | ............ | D21H 27/08 |
| 2017/0119226 A1* | 5/2017 | Nakayama | .............. | A47L 13/16 |

FOREIGN PATENT DOCUMENTS

| | | |
|---|---|---|
| JP | 2012-210790 A | 11/2012 |
| JP | 2014-114521 A | 6/2014 |

\* cited by examiner

NONWOVEN FABRIC, AND DUST COLLECTING FILTER, MEDIUM OF MICROORGANISM OR BIOLOGICAL TISSUE, AND COSMETIC ARTICLE, EACH HAVING THE SAME

BACKGROUND

1. Technical Field

The present disclosure relates to a nonwoven fabric having a fusion portion in which fibers are fused with each other, and a dust collecting filter, a medium for microorganisms or biological tissue, and a cosmetic article, using the nonwoven fabric.

2. Description of the Related Art

A nonwoven fabric has consecutive voids formed among fibers, and thus has a large surface area, and allows excellent ventilation or high permeability. Thus, the nonwoven fabric is used for various applications such as a dust collecting filter, medical applications, and cosmetic applications. For example, Japanese Patent Unexamined Publication No. 2012-210790 has proposed that a nonwoven fabric is used for cosmetic articles such as a face mask. Japanese Patent Unexamined Publication No. 2012-200152 has proposed that a nonwoven fabric is used for a medium for culturing species.

Generally, if a nonwoven fabric has a lot of voids therein, a surface area increases, and thus ventilation or permeability increases, but the strength (mechanical strength) decreases.

Japanese Patent Unexamined Publication No. 2014-114521 has proposed that composite nonwoven fabric C formed of nonwoven fabric A as a base and nanofiber nonwoven fabric layer B is laminated on nonwoven fabric D to which an adhesive is applied, as a nonwoven fabric for an air filter, from the viewpoint of increasing the strength of a filter using nanofibers and thus reducing a pressure loss.

SUMMARY

The present disclosure provides a nonwoven fabric having good strength, capable of being used for various applications.

A nonwoven fabric of the present disclosure contains a plurality of fibers having an average fiber diameter $D_{ave}$ in a range from 10 nm to 3 μm, inclusive. The nonwoven fabric has a plurality of fusion portions in which the plurality of fibers is fused together. The nonwoven fabric has a first principal surface and a second principal surface on an opposite side thereto. An average number Nh of the fusion portions observed per 500 μm² on the first principal surface is six or more.

A dust collecting filter of the present disclosure includes a porous base layer, a fiber layer laminated on the porous base layer, and a nonwoven fabric laminated on the porous base layer via the fiber layer. The nonwoven fabric contains a plurality of fibers having an average fiber diameter $D_{ave}$ in a range from 500 nm to 3 μm, inclusive, has a plurality of fusion portions in which the plurality of fibers is fused together, and has a first principal surface and a second principal surface on an opposite side thereto. An average number Nh of the fusion portions observed per 500 μm² on the first principal surface is six or more. The fiber layer includes fibers having an average fiber diameter smaller than the average fiber diameter $D_{ave}$ of the fibers contained in the nonwoven fabric.

A medium for microorganisms or biological tissue of the present disclosure includes a nonwoven fabric. The nonwoven fabric contains a plurality of fibers having an average fiber diameter $D_{ave}$ in a range from 0.8 μm to 3 μm, inclusive. The nonwoven fabric has a plurality of fusion portions in which the plurality of fibers is fused together. The nonwoven fabric has a first principal surface and a second principal surface on an opposite side thereto. Average number Nh of fusion portions observed per 500 μm² on the first principal surface is six or more.

A cosmetic article of the present disclosure includes a nonwoven fabric. The nonwoven fabric contains a plurality of fibers having an average fiber diameter $D_{ave}$ in a range from 10 nm to 800 nm, inclusive. The nonwoven fabric has a plurality of fusion portions in which the plurality of fibers is fused together. The nonwoven fabric has a first principal surface and a second principal surface on an opposite side thereto. An average number Nh of the fusion portions observed per 500 μm² on the first principal surface is six or more.

According to the present disclosure, it is possible to provide a nonwoven fabric having good strength and capable of being used for various applications.

DETAILED DESCRIPTION OF PREFERRED EMBODIMENTS

Prior to description of an embodiment of the present disclosure, a problem of a nonwoven fabric of the related art will be described briefly. If the mass per unit area of a nonwoven fabric is increased in order to increase strength of the nonwoven fabric, a pressure loss increases in a case where the nonwoven fabric is used for a dust collecting filter. Thus, if the mass per unit area of the nonwoven fabric is only increased, strength can be increased to some extent, but applications are restricted. If strength is increased by increasing the mass per unit area, a surface area is reduced. Thus, for example, in a medium application or cosmetic application such as a sheet mask (face mask or the like), culture efficiency is lowered, or permeability of beauty essence or skin lotion is deteriorated. As mentioned above, it is difficult to increase strength of the nonwoven fabric of the related art while maintaining characteristics necessary for each application.

(Nonwoven Fabric)

A nonwoven fabric related to the embodiment of the present disclosure contains a plurality of fibers having average fiber diameter $D_{ave}$, has a plurality of fusion portions in which the fibers are fused together, and has a first principal surface and a second principal surface on an opposite side thereto. Average number Nh of fusion portions observed per a first reference area on the first principal surface is six or more, and average fiber diameter $D_{ave}$ is in a range from 10 nm to 3 μm, inclusive. The first reference area is 500 μm².

The nonwoven fabric containing the fibers indicates that the fibers are contained as main components. In this case, the content of the main components is 80% by weight or greater.

Generally, the nonwoven fabric has a large surface area, and allows excellent ventilation, and high permeability of a liquid due to consecutive voids formed among the fibers, and is used for various applications. If the consecutive voids increases (fibers are coarse), a surface area increases, and ventilation or permeability increases, but mechanical strength of the nonwoven fabric is reduced. However, if the mass per unit area of the nonwoven fabric is increased, the strength increases, but the fibers become dense, and thus the number of consecutive voids is reduced. Thus, performance necessary in each application cannot be obtained. For example, since a pressure loss increases, the nonwoven fabric is not suitable for a dust collecting filter application.

The nonwoven fabric according to the present embodiment contains a plurality of fibers having average fiber diameter $D_{ave}$ in a range from 10 nm to 3 μm, inclusive. Average number Nh of fusion portions in which fibers are fused together is six or more per a first reference area (500 μm²) on the first principal surface of the nonwoven fabric. As mentioned above, if a lot of fusion portions are formed, high strength can be ensured, and a lot of consecutive voids can be secured among the fibers of the nonwoven fabric. Thus, it is possible to increase the strength of the nonwoven fabric while maintaining characteristics necessary in various applications, for example, a large surface area, ventilation, and permeability. For example, in a dust collecting filter application, both of high strength and low pressure loss can be achieved.

The fusion portion is a portion in which fibers forming the nonwoven fabric are fused together and are thus integrally formed through, for example, welding or fusion, and has the same state as a state formed through the welding or the fusion.

Average number Nh of fusion portions may be obtained by counting and summing the number of fusion portions in a plurality of regions (for example, ten locations) each having a predetermined area on the first principal surface, and converting the number thereof into the number per the first reference area, in a scanning electron microscope observation image (SEM image) which is captured in a state of facing the first principal surface of the nonwoven fabric. In a case where average number Nh is obtained, the fusion portions are counted in a region in which integrally formed fibers are clearly checked when the nonwoven fabric is viewed from the first principal surface.

Average fiber diameter $D_{ave}$ indicates an average value of diameters of the fibers. The diameter of the fiber is a width in a direction perpendicular to a length direction of the fiber when viewed from the normal direction of the first principal surface. Average fiber diameter $D_{ave}$ is an average value of diameters of, for example, any ten fibers contained in the nonwoven fabric at any locations (excluding the fusion portion).

In 70% or more of fusion portions observed per the first reference area, maximum length $L_{max}$ of the fusion portions and average fiber diameter $D_{ave}$ preferably satisfy $L_{max} \geq D_{ave}$. As mentioned above, a large fusion portion is formed, and thus it is possible to further increase strength of the nonwoven fabric. Maximum length $L_{max}$ is the maximum length of the fusion portion when the first principal surface is viewed from the normal direction. A proportion (%) of fusion portions satisfying $L_{max} \geq D_{ave}$ is an average value calculated for a plurality of (for example, ten) any regions.

Average number Np of fusion portions observed per a second reference area of a cross-section perpendicular to the first principal surface of the nonwoven fabric preferably satisfies Np>Nh. Here, the second reference area is 500 μm². As mentioned above, if the number of fusion portions in the normal direction of the first principal surface is larger than the number of fusion portions in the surface direction, it is possible to increase strength in the normal direction. As a result, it is possible to suppress peeling among fibers in the normal direction. Elasticity of the nonwoven fabric in the surface direction can also be easily ensured.

For example, average number Np of fusion portions may be obtained in the same manner as average number Nh in an SEM image of a cross-section perpendicular to the first principal surface of the nonwoven fabric. In a case where average number Np is obtained, the fusion portions may be counted in a region in which integrally formed fibers are clearly checked when the fusion portions are viewed from the section.

Hereinafter, a configuration of the nonwoven fabric will be described in more detail. Materials of the fibers (first fibers) forming the nonwoven fabric are not particularly limited, and may include, for example, polymers such as polyamide (PA), polyimide (PI), polyamideimide (PAI), polyetherimide (PEI), polyacetal (POM), polycarbonate (PC), polyether ether ketone (PEEK), polysulfone (PSF), polyethersulfone (PES), polyphenylene sulfide (PPS), polytetrafluoroethylene (PTFE), polyarylate (PAR), polyacrylonitrile (PAN), polyvinylidene fluoride (PVDF), polystyrene (PS), polyvinyl alcohol (PVA), polyvinyl acetate (PVAc), polypropylene, polyester (polylactic acid, polyethylene terephthalate (PET), and the like), polyurethane (PU), and cellulose derivatives. Each of such polymers includes both a homopolymer and a copolymer. The fibers may contain one kind of such materials, or two or more kinds thereof. Materials may be selected depending on an application of the nonwoven fabric. Among the materials, PS and/or PU are (is) preferably used from the viewpoint of easily increasing the strength of the nonwoven fabric. Above all, PU has self-fusion property and easily forms a lot of fusion portions, and is thus preferably used.

The nonwoven fabric is formed according to, for example, an electrostatic spinning method. More specifically, a raw material liquid of fibers is discharged from a nozzle of an electrostatic spinning mechanism so as to form fibers, and the fibers are accumulated on a principal surface of a base layer so that the nonwoven fabric is formed. At this time, in a portion where the fibers are in contact with each other, materials of the fibers are mutually diffused so as to be integrated, and thus a fusion portion is formed. In other words, the fusion portion is formed in a state in which shapes of the fibers are not fixed, and the fibers have partial flowability. The number of fusion portions may be adjusted by adjusting, for example, solid content concentration of a raw material liquid, and humidity, temperature, and/or intensity of an electric field when spinning is performed. Such conditions will be described more in detail in the item of Nonwoven Fabric Manufacturing Method which will be described later.

Average fiber diameter $D_{ave}$ of the fibers may be 10 nm or more, may be 50 nm or more or 100 nm or more, and may be 700 nm or more (for example, 800 nm or more) or 1 μm or more. Average fiber diameter $D_{ave}$ may be 3 μm or less, and may be 2.5 μm or less (for example, 2 μm or less), or 800 nm or less. The lower limit values and the upper limit values may be optionally combined with each other. Average fiber diameter $D_{ave}$ may be in a range, for example, from 10 nm to 2.5 μm, from 10 nm to 2 μm, from 0.7 μm to 3 μm, from 0.7 μm to 2.5 μm, from 0.8 μm to 3 μm, from 1 to 3 μm, from 10 to 800 nm, from 50 to 800 nm, or form 100 to 800 nm, all inclusive.

If the fibers have such an average fiber diameter, the strength of the nonwoven fabric as an aggregate of the fibers is easily ensured, and a lot of consecutive voids are easily formed among the fibers in the nonwoven fabric. Even if a laminated nonwoven fabric is not formed by laminating a base layer or a protection layer, a self supporting film can be easily configured by only the nonwoven fabric.

Average fiber diameter $D_{ave}$ may be selected as appropriate from the ranges depending on applications. The nonwoven fabric may be used as an ultrafine fiber layer which functions as a dust collecting layer, for example, in a dust collecting filter application. The nonwoven fabric may be used as a layer (protection layer) protecting the ultrafine fiber layer used as a dust collecting layer. Average fiber diameter $D_{ave}$ may be determined as appropriate from a range, for example, from 10 nm to 800 nm, inclusive in a case of the former ultrafine fiber layer, and may be determined as appropriate from a range, for example, from 500 nm to 3 μm, inclusive in a case of the latter protection layer. In an application to a medium for a microorganism or biological tissue, average fiber diameter $D_{ave}$ may be, for example, in a range from 0.8 μm to 3 μm, inclusive, or from 1 μm to 3 μm, inclusive. A medium using the nonwoven fabric having such average fiber diameter $D_{ave}$ is suitable also for research and development applications in a medical field and/or a pharmaceutical field. In a cosmetic article application, average fiber diameter $D_{ave}$ may be, for example, in a range from 10 nm to 800 nm, inclusive, and may be in a range from 100 nm to 800 nm, inclusive.

The nonwoven fabric has the first principal surface and the second principal surface opposite thereto. The first principal surface is typically an upper surface when a nonwoven fabric is formed according to an electrostatic spinning method, that is, an upper principal surface in a direction in which fibers are accumulated (a principal surface on an opposite side to a base layer).

Average number Nh of fusion portions observed per the first reference area (500 μm$^2$) on the first principal surface is six or more, and is preferably eight or more. An upper limit of average number Nh of fusion portions is not particularly limited, but average number Nh thereof is preferably fifty or less from the viewpoint of easily ensuring growth to some extent in the surface direction. If average number Nh of fusion portions is less than six, strength of the nonwoven fabric is insufficient, and thus a self supporting film is hardly formed.

The fusion portion preferably has some size from the viewpoint of further increasing strength of the nonwoven fabric. From this viewpoint, in 70% or more (preferably, 80% or more) of fusion portions observed per the first reference area (500 μm$^2$) on the first principal surface, maximum length $L_{max}$ of the fusion portions and average fiber diameter $D_{ave}$ preferably satisfies $L_{max} \geq 0.8\ D_{ave}$, and is more preferably $L_{max} \geq D_{ave}$.

In the electrostatic spinning method, fibers spun from a raw material liquid are accumulated on a principal surface of a base layer disposed on an electrode, and thus a nonwoven fabric is formed. In the fibers right after being spun, a solvent which remains in a very small amount when the fibers have been accumulated on the principal surface of the base layer rapidly volatilizes, but, if accumulation of the fibers progresses, volatilization of the solvent does not catch up with accumulation, and thus an amount of the remaining solvent increases. Consequently, fibers are melted via the remaining solvent, and thus a fusion portion is easily formed.

In a section (that is, a cross-section perpendicular to the first principal surface of the nonwoven fabric) in a thickness direction of the nonwoven fabric, average number Np of fusion portions observed per a second reference area (500 μm$^2$) preferably satisfies Np>Nh, and more preferably satisfies Np≥1.5 Nh or Np≥2 Nh. In a case where Np and Nh satisfy the relationship, it is possible to increase strength of the nonwoven fabric in the thickness direction. In the present disclosure, the number of coupling portions can be controlled to be increased in the thickness direction more than in the surface direction. Details of the reason are not clear, but, since fibers mounted on the base layer in the surface direction are charged to the same polarity when the nonwoven fabric is manufactured, fibers are made to hardly overlap each other by controlling charged states thereof. On the other hand, fibers accumulated in the thickness direction are more easily influenced by the gravity of the fibers than by a repulsive force between the fibers and the fibers in the under layer in contact therewith. Therefore, it is considered that fusion portions in which fibers overlap each other in the thickness direction can be easily formed relatively.

A thickness of the nonwoven fabric may be selected as appropriate from a range of, for example, 1 to 300 μm, and may be 10 to 200 μm depending on applications. In a case where the thickness of the nonwoven fabric is 50 μm or more, high strength is easily obtained. Thus, the nonwoven fabric can be used as a self supporting film without laminating a base layer and/or a protection layer.

The thickness of the nonwoven fabric is, for example, an average value of thicknesses measured at a plurality of any (for example, ten) locations in the nonwoven fabric. The thickness of the nonwoven fabric is a distance between two principal surfaces of the nonwoven fabric. The thickness of the nonwoven fabric may be specifically obtained as follows. First, in a section picture of the nonwoven fabric, a line perpendicular to the first principal surface is drawn from any one point on the first principal surface to the second principal surface. Among fibers on the line, a distance between outsides of two fibers which are most distant from each other is obtained as the thickness of the nonwoven fabric. This is similarly performed on a plurality of any other points (for example, nine points) so that thicknesses of the nonwoven fabric are measured, and a numerical value obtained by averaging the thicknesses is used as the thickness of the nonwoven fabric.

The mass per unit area of the nonwoven fabric may be selected from a range of, for example, 0.1 to 500 g/m$^2$ depending on applications. In the present embodiment, since the nonwoven fabric includes a lot of fusion portions, even if the mass per unit area of the nonwoven fabric is relatively small as 1.5 g/m$^2$ or more, the strength of the nonwoven fabric can be increased, and thus the nonwoven fabric can also be used as a self supporting film.

(Manufacturing Method of Nonwoven Fabric)

The nonwoven fabric (first nonwoven fabric) may be manufactured by spinning a raw material liquid of fibers according to an electrostatic spinning (electrospinning) method, and accumulating obtained fibers on a base layer so as to form fusion portions.

Hereinafter, each step will be described more in detail.

(Electrostatic spinning step)

In the electrostatic spinning step, the raw material liquid is electrostatically spun on one principal surface of the base layer so that fibers are accumulated thereon, and thus the nonwoven fabric (first nonwoven fabric) is manufactured. In the electrostatic spinning, the fibers are generated by applying a high voltage to the raw material liquid, and ejecting the raw material liquid having electric charge from a nozzle.

As a raw material of the fibers, a variety of polymers exemplified as the materials of the fibers are used. Precursors of the polymers may be used as the raw material. For example, in a case where the fibers are formed of PI, a PI precursor such as a polyamic acid may be used as the raw material.

The raw material liquid typically contains a solvent in addition to the raw material of the fibers. A solvent is not particularly limited as long as the solvent can dissolve a raw material of fibers and can be removed through volatilization, and may be appropriately selected from water and an organic solvent depending on the type of raw material or a manufacturing condition. As the solvent, an aprotic polar organic solvent is preferably used. Examples of the solvent may include amides (chain or cyclic amides) such as N,N-dimethylformamide (DMF), N,N-dimethylacetamide (DMAc), N-methyl-2-pyrrolidone (NMP); and sulfoxides such as dimethyl sulfoxide. The solvent may be used alone or in combination of two or more kinds thereof. Amides such as DMAc and DMF are preferably used from the viewpoint that a raw material such as PS or PU is easily dissolved, and electrostatic spinning is easily performed. The raw material liquid may contain a well-known additive as necessary.

In a case where the nonwoven fabric is formed by using a solution containing the raw material of fibers as a raw material liquid, if the fibers are accumulated in a state in which a solvent remains in the fibers, the fibers are welded together due to action of the remaining solvent at contact points among the fibers, and thus fusion portions are formed. In controlling the number or sizes of fusion portions, and a distribution state of the fusion portions, it is important to adjust solid content concentration of the raw material liquid or humidity during spinning.

The solid content concentration of the raw material liquid may be adjusted depending on a solvent or the kind of raw material of fibers, but is, for example, 5% to 50% by mass, inclusive, and is preferably 10% to 30% by mass.

The humidity during spinning is, for example, 20 to 80% Rh, and is preferably 30 to 50% Rh.

It is also effective to adjust temperature in order to cause a state in which the solvent appropriately remains in the fibers when fusion portions are formed. The temperature of a spinning space is preferably, for example, 20° C. to 50° C., and is also preferably 25° C. to 35° C.

From the viewpoint of adjusting a charging ratio of spun fibers or an amount of a remaining solvent when fibers are accumulated, it is also preferable to adjust intensity of an electric field during electrostatic spinning. The intensity of an electric field may be adjusted by adjusting, for example, a distance between the nozzle from which the raw material liquid is ejected and the base layer (collector) on which fibers are accumulated. The distance between the nozzle and the collector is, for example, 100 to 600 mm, and is preferably 200 to 300 mm.

The nonwoven fabric obtained through the electrostatic spinning is dried by using a heater or the like. The solvent remaining in the fibers is removed through this drying process. At this time, the solvent is removed at the contact points in a state in which the fibers are melted via the solvent, and thus fusion portions where the fibers are integrated with each other are formed. The nonwoven fabric may be dried in the electrostatic spinning step, and may be dried in a step (drying step) separate from the electrostatic spinning step. The drying temperature may be selected as appropriate depending on a material of the fibers or the kind of solvent, and is, for example, 20° C. to 150° C., and is preferably 40° C. to 100° C.

In a case where the nonwoven fabric is formed on the base layer, a resin film or the like may be used as the base layer, but a porous base layer such as a nonwoven fabric (second nonwoven fabric) is preferably used. Materials of fibers (second fibers) contained in the second nonwoven fabric are not particularly limited, and may include, for example, glass fibers, cellulose, acrylic resin, polyolefin, polyester, or PA. Examples of polyolefin may include PP and polyethylene. Examples of polyester may include PET and polybutylene terephthalate. The second fibers may contain one kind of such materials, or two or more kinds thereof. Among the materials, cellulose, polyester, and/or PA is preferably used from the viewpoint of holding the shape.

An average fiber diameter of the second fibers is not particularly limited, and is, for example, 1 µm to 400 µm. The second nonwoven fabric is manufactured by using, for example, a spun bonding method, a dry method (for example, an air RAID method), a wet method, a melt blow method, a needle punch method. A thickness of the second nonwoven fabric is, for example, 50 to 500 µm. A nonwoven fabric (first nonwoven fabric) is formed by using a releasable sheet as a base layer, and the first nonwoven fabric may be formed as a result of being peeled off from the sheet.

In a case where a laminated nonwoven fabric including the nonwoven fabric according to the present embodiment is manufactured, a pressing step may be provided as necessary. In the pressing step, for example, a laminate including the base layer and the first nonwoven fabric is compressed in a thickness direction, and thus the respective layers can be pressed. A well-known pressing member such as a roller may be used for the pressing.

The nonwoven fabric (first nonwoven fabric) may be manufactured by, for example, a manufacturing apparatus which conveys the base layer (second nonwoven fabric) from an upstream side to a downstream side of a manufacturing line, and forms the nonwoven fabric (first nonwoven fabric) on a principal surface of the base being conveyed.

Figure 1:
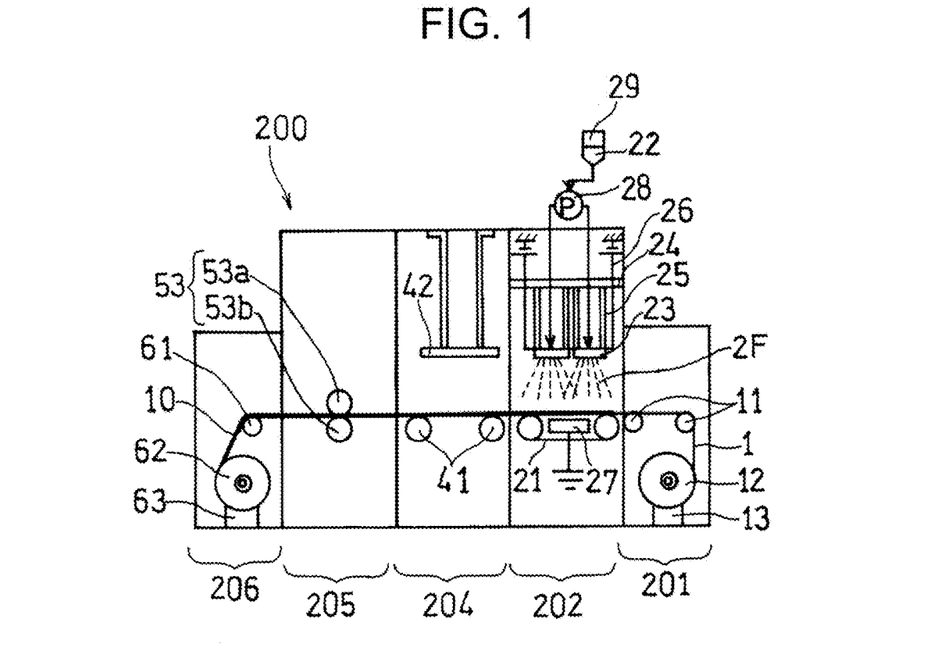
FIG. 1 is a diagram schematically illustrating a configuration of an example of a manufacturing apparatus manufacturing a nonwoven fabric related to an embodiment of the present disclosure.

Hereinafter, with reference to FIG. 1, a description will be made of manufacturing apparatus (system) 200 of the nonwoven fabric, but the following manufacturing apparatus 200 do not limit the present disclosure. FIG. 1 is a diagram schematically illustrating a configuration of an example of manufacturing apparatus 200. FIG. 1 illustrates a case where laminated nonwoven fabric 10 in which base layer 1 and a nonwoven fabric (first nonwoven fabric) are laminated in this order is formed.

The manufacturing apparatus includes, for example, (1) base layer feeding device 201 which feeds base layer 1 to the manufacturing line, and (2) electrostatic spinning device 202 which generates first fibers by subjecting raw material liquid 22 containing a raw material of the first fibers to electrostatic spinning, and accumulates the first fibers on base layer 1 so as to form the first nonwoven fabric. The manufacturing apparatus may further include (3) drying unit 204. The manufacturing apparatus may include (4) pressure bonding part 205 which presses a laminate including the base layer 1 and the first nonwoven fabric. In a case where a releasable sheet is used as base layer 1, base layer 1 may be peeled off from the formed first nonwoven fabric.

First, base layer 1 is prepared, and is conveyed from the upstream side of the manufacturing line of manufacturing apparatus 200 to the downstream side thereof. Base material layer feeding device 201 which accommodates therein base layer 1 wound in a roll form is provided on the most upstream side of manufacturing apparatus 200. Base material layer feeding device 201 rotates feed reel 12 with motor 13 so as to feed base layer 1 wound on feed reel 12 to conveyance rollers 11 of the manufacturing line.

Base material layer 1 is conveyed to electrostatic spinning device 202 including an electrostatic spinning unit (not illustrated) by conveyance rollers 11. The electrostatic spinning mechanism provided in the electrostatic spinning unit includes discharger (nozzle) 23 which is provided on an upper side in the apparatus and discharges raw material liquid 22 containing a raw material of the first fibers, a charger (which will be described later) which positively charges discharged raw material liquid 22, and conveyance conveyer 21 which is disposed to face discharger 23 and conveys base layer 1 from the upstream side to the downstream side. Conveyance conveyer 21 functions as a collector which collects first fibers 2F along with base layer 1. The number of electrostatic spinning units is not particularly limited, and may be one, or two or more.

In a case where there are a plurality of electrostatic spinning units and/or dischargers 23, an average fiber diameter of first fibers 2F to be formed may be changed for each electrostatic spinning unit or for each discharger 23, as necessary. The average fiber diameter of first fibers 2F may be changed by adjusting ejection pressure of the raw material liquid, an applied voltage, concentration of the raw material liquid, a distance from discharger 23 to base layer 1, temperature, humidity, and the like.

A plurality of discharge outlets (not illustrated) of raw material liquid 22 is provided on a side of discharger 23 facing the principal surface of base layer 1. Discharger 23 is supported by second support 25 in such a manner that its own longitudinal direction is parallel to the principal surface of base layer 1. Second support 25 is provided above the electrostatic spinning unit, and extends downwardly from first support 24 parallel to the conveyance direction of base layer 1. First support 24 may be movable so that discharger 23 is swung in a direction perpendicular to the conveyance direction of base layer 1.

The charger is formed of voltage applying device 26 applying a voltage to discharger 23, and counter electrode 27 provided to be parallel to conveyance conveyer 21. Counter electrode 27 is grounded (connected to the ground). Consequently, a potential difference (for example, 20 kV to 200 kV) corresponding to the voltage applied by voltage applying device 26 can be caused between discharger 23 and counter electrode 27. The configuration of the charger is not particularly limited. For example, counter electrode 27 may be negatively charged. The belt portion of conveyance conveyer 21 may be formed of a conductor instead of providing counter electrode 27.

Discharger 23 is formed of a conductor and has a long shape, and a cavity is provided therein. This cavity functions as an accommodator accommodating raw material liquid 22 therein. Raw material liquid 22 is supplied from raw material liquid tank 29 to the cavity of discharger 23 by a pressure produced by pump 28 communicating with the cavity of discharger 23. Raw material liquid 22 is discharged from the discharge outlet toward the principal surface of base layer 1 by the pressure produced by pump 28. Discharged raw material liquid 22 causes electrostatic explosion to produce a fibrous material (first fibers 2F) during movement in a charged state in a space (generation space) between discharger 23 and base layer 1. Generated first fibers 2F are accumulated on the principal surface of base layer 1 so as to form the first nonwoven fabric.

A configuration of the electrostatic spinning mechanism is not limited to the above-described configuration. A mechanism can be used without being particularly limited as long as the mechanism can generate first fibers 2F from raw material liquid 22 by electrostatic force in a generation space of predetermined fibers, and can accumulate generated first fibers 2F on the principal surface of base layer 1. The nozzle forming discharger 23 is not particularly limited, and may be, for example, a V-shaped nozzle whose shape of a cross-section perpendicular to the longitudinal direction of discharger 23 is gradually reduced downward from the top, or a needle-type nozzle.

First nonwoven fabric 2 may be dried in electrostatic spinning device 202 so that a solvent remaining first fibers 2F is removed, but may be dried by drying unit 204 subsequent to electrostatic spinning device 202. Fusion portions are formed through this drying process. Drying unit 204 is provided with heater 42. In other words, first nonwoven fabric 2 is dried by heater 42 while being conveyed by conveyance roller 41. However, there is no limitation thereto, and the first nonwoven fabric may be dried according to a decompression method.

Next, in pressure bonding part 205, a laminate in which the first nonwoven fabric is laminated on base layer 1 is interposed and pushed between a pair of pressing rollers 53 (pressing rollers 53a and 53b) which are provided in pressure bonding part 205 and are vertically disposed. Consequently, laminated nonwoven fabric 10 is formed.

Finally, laminated nonwoven fabric 10 is conveyed from pressure bonding part 205, and is then conveyed to collecting device 206 which is disposed on the further downstream side, via roller 61. For example, collecting device 206 has therein collecting reel 62 for winding conveyed laminated nonwoven fabric 10 thereon. Collecting reel 62 is rotatably driven by motor 63.

In a case where a releasable sheet is used as base layer 1, base layer 1 may be peeled off from laminated nonwoven fabric 10 obtained in pressure bonding part 205 so as to be wound and collected by a collecting reel or the like, and the first nonwoven fabric peeled off from base layer 1 may be conveyed from pressure bonding part 205 so as to be collected by collecting device 206.

The nonwoven fabric according to the present embodiment has a lot of consecutive voids and also good strength, and can thus be used for various applications. The nonwoven fabric is suitable for, particularly, a dust collecting filter, a medium for microorganisms or biological tissue, and a cosmetic article such as a sheet mask.

(Dust Collecting Filter)

A dust collecting filter may be formed of only the above-described nonwoven fabric (first nonwoven fabric), and may include a porous base layer and the first nonwoven fabric laminated on the porous base layer. The porous base layer is an aggregate and often has substantially no dust collection function. The dust collecting filter includes the first nonwoven fabric, and can thus reduce a pressure loss and can capture dust.

Figure 2:
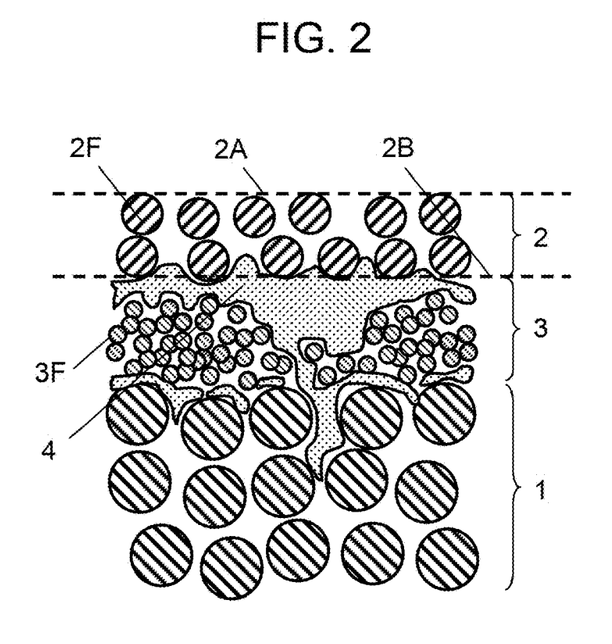
FIG. 2 is a conceptual sectional view illustrating an example of a dust collecting filter according to the embodiment of the present disclosure.

A fiber layer including fibers having an average fiber diameter smaller than average fiber diameter $D_{ave}$ may be provided between the porous base layer and the first nonwoven fabric. In a case where such a fiber layer is included, smaller dust can be captured by the fiber layer. FIG. 2 is a conceptual sectional view illustrating an example of dust collecting filter 30 according to the embodiment of the present disclosure. Dust collecting filter 30 includes porous base layer 1, fiber layer 3 laminated on base layer 1, and first nonwoven fabric 2 laminated on base layer 1 via fiber layer 3. First nonwoven fabric 2 contains first fibers 2F having average fiber diameter $D_{ave}$ in a range from 500 nm to 3 μm, inclusive, has a plurality of fusion portions among first fibers 2F, and has first principal surface 2A and second principal surface 2B on an opposite side thereto. Average number Nh of the fusion portions observed per 500 μm² on first principal surface 2A is six or more. Fiber layer 3 contains fibers (third fibers) 3F having an average fiber diameter smaller than average fiber diameter $D_{ave}$ of first fibers 2F. The respective layers may be adhered to each other via adhesive 4 as necessary.

Materials of fibers 3F forming fiber layer 3 may be selected as appropriate from among the materials exemplified with respect to first fibers 2F. Fiber layer 3 may be formed according to an electrostatic spinning method in the same manner as first nonwoven fabric 2. However, a fusion portion as in the case of first nonwoven fabric 2 may not be necessarily formed in fiber layer 3, and the number thereof may be small even in a case where the fusion portions are formed.

The average fiber diameter of fibers 3F may be adjusted by adjusting ejection pressure of a raw material liquid, an applied voltage, concentration of the raw material liquid, a distance from the discharger to the base layer, temperature, humidity, and the like. The average fiber diameter of fibers 3F may be smaller than average fiber diameter $D_{ave}$, may be selected as appropriate in a range from 5 nm to 900 nm, inclusive, for example, and may be equal to or more than 10 nm and less than 500 nm. In a case where fiber layer 3 is provided, first nonwoven fabric 2 functions as a layer protecting fibers 3F, and average fiber diameter $D_{ave}$ of first nonwoven fabric 2 may be determined as appropriate from a range in a range from 500 nm to 3 μm, inclusive, as described above according to the average fiber diameter of fibers 3F.

The dust collecting filter may be formed of a porous base layer, a first nonwoven fabric laminated on the porous base layer, and a protection layer laminated on the first nonwoven fabric. In this case, the first nonwoven fabric is formed of ultrafine fibers as described above. The respective layers may be adhered to each other via an adhesive as necessary.

In a case where the dust collecting filter is formed of a laminate including the porous base layer, the first nonwoven fabric, and the protection layer, average fiber diameter $D_{ave}$ of the first nonwoven fabric may be determined as appropriate from a range in a range from 10 nm to 800 nm, inclusive as described above. The protection layer may be formed of a third nonwoven fabric containing fourth fibers. A material of the fourth fibers is not particularly limited, and may be selected as appropriate from among the materials exemplified with respect to the second fibers. PP is preferably used from the viewpoint that the material is easily charged.

An average fiber diameter of the fourth fibers is not particularly limited, but may be larger than average fiber diameter $D_{ave}$. The average fiber diameter of the fourth fibers is, for example, 500 nm to 20 μm, and may be 1 μm to 20 μm.

A manufacturing method of the third nonwoven fabric is not particularly limited, and the methods exemplified in the second nonwoven fabric may be exemplified in the same manner. Above all, the third nonwoven fabric is preferably manufactured by using a melt blow method from the viewpoint that it is easy to form a nonwoven fabric having a small fiber diameter appropriate for the dust collecting filter.

(Medium of Microorganism or Biological Tissue)

The nonwoven fabric (first nonwoven fabric) may be used also as a medium (a scaffold for culture) for culturing microorganisms or biological tissue. In the related art, a medium such as agar or gelatin is used. However, in the medium of the related art, culturing can be performed in a surface direction, but it is difficult to perform three-dimensional culturing.

The first nonwoven fabric has a lot of consecutive voids, and can thus culture microorganisms or biological tissue in a three-dimensional manner. The first nonwoven fabric may be impregnated with a liquid containing nutrients or a gel-like medium in a large amount. The first nonwoven fabric has high strength and also elasticity to some extent in a surface direction, and is thus excellent in practical use.

(Cosmetic Article)

Regarding cosmetic articles using the nonwoven fabric, for example, the nonwoven fabric is used as a sheet mask (or a sheet pack) or the like which is impregnated with skin lotion or beauty essence, and covers the entire face, or a part of the face or the body (the hand, the foot, and the like). In this application, it is required for the nonwoven fabric to be highly impregnated with skin lotion or beauty essence, to have high affinity for the skin, and to have high strength when the nonwoven fabric is adhered to the skin or peeled off from the skin. The first nonwoven fabric has a lot of consecutive voids, and thus is highly impregnated with a liquid such as skin lotion or beauty essence. The first nonwoven fabric includes a lot of fusion portions, and thus has high strength. Thus, the first nonwoven fabric is appropriately used also for cosmetic articles such as a sheet mask (for example, a face mask).

Particularly, in the first nonwoven fabric, in a case where average number Np of fusion portions is larger than average number Nh thereof, it is possible to ensure strength and to reduce friction against the skin since the number of fusion portions is small in the surface direction. Therefore, such a first nonwoven fabric is suitable for cosmetic articles such as, particularly, a sheet mask. In this application, a relationship of Np≥1.5 Nh or Np≥2 Nh is more preferably satisfied.

EXAMPLES

Hereinafter, the present embodiment will be described in detail on the basis of Examples, but the present disclosure is not limited to the following Examples.

Example 1

(1) Manufacturing of Nonwoven Fabric

A nonwoven fabric composed mainly of cellulose (thickness: 300 μm, average fiber diameter: 15 μm, and mass per unit area: 42 g/m²) is prepared as base layer 1.

By using manufacturing system 200 illustrated in FIG. 1, first fibers 2F are accumulated on conveyed base layer 1 so as to form the first nonwoven fabric, and thus laminated nonwoven fabric 10 is manufactured. As a raw material liquid of first fibers 2F, a DMAc solution containing 20% by mass of PU is used. Average fiber diameter $D_{ave}$ of the first nonwoven fabric is 0.8 μm, an average thickness thereof is 20 μm, and the average mass per unit area thereof is 10 g/m².

Figure 3:
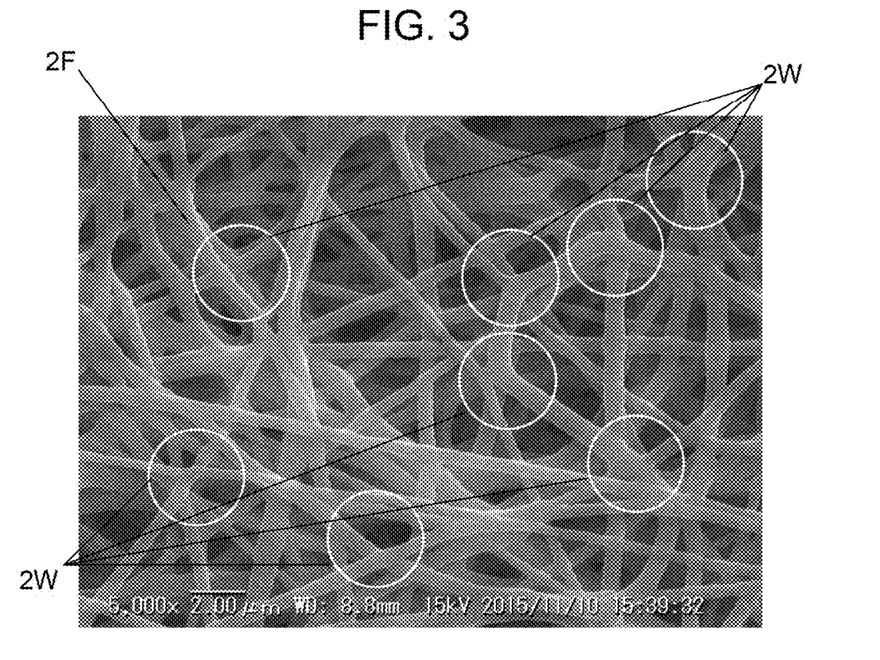
FIG. 3 is a diagram illustrating a scanning electron microscope (SEM) observation image, captured from a first principal surface side of a nonwoven fabric obtained in Example 1 of the present disclosure.

In first nonwoven fabric 2, a SEM image is captured from a principal surface (first principal surface) on an opposite side to base layer 1, and average number Nh of fusion portions is obtained as eight according to the above-described procedures. FIG. 3 illustrates a SEM image captured from the first principal surface. Portions surrounded by circles in FIG. 3 are fusion portions 2W among first fibers 2F.

A SEM image of a cross-section perpendicular to the first principal surface of first nonwoven fabric 2 is captured, and average number Np and $L_{max}$ of fusion portions 2W are respectively obtained as twenty and 1 μm according to the above-described procedures.

(2) Evaluation of Strength (a) Tape Peeling Test

A sticky tape having adhesive force of 5 N/cm is attached to the first principal surface of first nonwoven fabric 2 of laminated nonwoven fabric 10 obtained in the above (1), and one end of the sticky tape is raised so that the sticky tape is peeled off at a peeling angle of 180°. At this time, only the sticky tape is peeled off, and first nonwoven fabric 2 remains on base layer 1 and thus peeling of first nonwoven fabric 2 is not observed. It can be seen therefrom that first nonwoven fabric 2 has peeling-off strength higher than 5 N/cm and thus has high strength.

(b) Peeling Test of First Nonwoven Fabric

Figure 4:
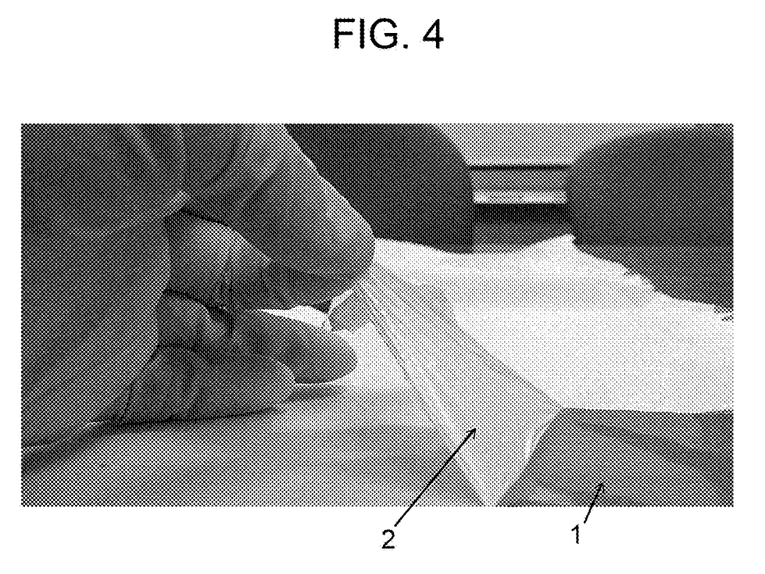
FIG. 4 is a diagram illustrating an observation image when the nonwoven fabric obtained in Example 1 of the present disclosure is peeled off from a base layer.

Laminated nonwoven fabric 10 is manufactured in the same manner as in the above (1) except that a PET film is used as base layer 1. The extent of fracture of first nonwoven fabric 2 when first nonwoven fabric 2 is peeled off from base layer 1 is checked. FIG. 4 is a picture when first nonwoven fabric 2 is peeled off from base layer 1. As illustrated in FIG. 4, when first nonwoven fabric 2 is peeled off from base layer 1, first nonwoven fabric 2 is pulled by a strong force causing wrinkles in a pulling direction, but fracture of first nonwoven fabric 2 is not observed. Thus, it can be seen that first nonwoven fabric 2 has high strength.

Example 2

(1) Manufacturing of Nonwoven Fabric

A nonwoven fabric composed mainly of cellulose (thickness: 300 μm, average fiber diameter: 15 μm, and mass per unit area: 42 g/m$^2$) is prepared as base layer 1.

A laminated nonwoven fabric having a three-layer structure is manufactured by using a manufacturing apparatus which includes the same electrostatic spinning device as electrostatic spinning device 202 between base layer feeding device 201 and electrostatic spinning device 202, and includes an adhesive spraying device between the electrostatic spinning device and electrostatic spinning device 202, in manufacturing apparatus 200 illustrated in FIG. 1.

More specifically, third fibers are accumulated on conveyed base layer 1 by using a DMAc solution containing PES at a concentration of 20% by mass as a raw material liquid, and thus a fiber layer is formed. An adhesive (a polyester-based hot melt resin) is sprayed onto the obtained fiber layer, then, the first fibers are accumulated thereon in the same conditions as in Example 1 so that the first nonwoven fabric is formed, and thus a laminate is formed. As raw material liquid 22 of the first fibers, a DMAc solution containing 20% by mass of PU is used. An average fiber diameter of the fiber layer is 200 nm, and an average thickness thereof is 10 μm. Average fiber diameter $D_{ave}$ of the first nonwoven fabric is 800 nm, and an average thickness thereof is 150 μm. The obtained laminate is heated so that the adhesive is melted, then, the laminate is fed between a pair of pressing rollers, and is pushed in a thickness direction under the pressure of 5 kPa so as to be pressed, and thus the laminated nonwoven fabric is manufactured.

(2) Pressure Loss

The laminated nonwoven fabric obtained in the above (1) is cut into a piece with a size of height 12 cm×width 12 cm, and thus a sample is manufactured. Atmospheric dust is sucked to the sample at a surface wind speed of 5.3 cm/sec. Air pressure $P_0$ on the upstream side and air pressure $P_1$ on the downstream side of the sample at this time are measured, and a pressure loss (=$P_0$-$P_1$) is calculated and found to be 35 Pa which is lower than a general value of 50 Pa. The pressure loss is measured on the basis of the regulations of JIS B 9908, Form 1. In the test method in the Form 1, a pressure loss is measured as follows. A filter unit having laminated nonwoven fabric is held in a unit fixer without leakage of air. A static pressure measurer is attached to the filter unit. The static pressure measurer includes straight tubes sandwiching the filter unit therebetween, and the straight tubes are provided with static pressure measurement holes, respectively, perpendicular to tube walls on an upstream side and a downstream side. In this state, a blower sends wind to the filter unit in a rated air volume. The static pressure on the upstream side and that on the downstream side are measured by manometers which are connected to the static pressure measurement holes via the tubes, respectively, and thus the pressure loss is obtained.

Example 3

(1) Manufacturing of Nonwoven Fabric

A nonwoven fabric composed mainly of cellulose (thickness: 300 μm, average fiber diameter: 15 μm, and mass per unit area: 42 g/m$^2$) is prepared as base layer 1.

By using manufacturing system 200 illustrated in FIG. 1, first fibers 2F are accumulated on conveyed base layer 1 so as to form the first nonwoven fabric, and thus laminated nonwoven fabric 10 is manufactured. As raw material liquid 22 of first fibers 2F, a DMAc solution containing 20% by mass of PU is used. Average fiber diameter $D_{ave}$ of the first nonwoven fabric is 200 nm, and an average thickness thereof is 20 μm.

(2) Evaluation

Obtained laminated nonwoven fabric 10 is cut into a piece with a size of 5 cm×5 cm, and is impregnated with beauty essence available in the market so that a sheet mask is manufactured. This sheet mask is adhered to the cheek so that a surface to which the first nonwoven fabric is exposed is brought into contact with the cheek. After five minutes, the sheet mask is peeled off from the cheek. The sheet mask causes less resistance to the skin when adhered to or peeled off from the skin, and feels soft. Remaining fibers are not observed on a surface of the cheek after the sheet mask is peeled off from the cheek, and thus the sheet mask has high strength.

The nonwoven fabric of the present disclosure may be used for a dust collecting filter or a filter medium of an air purifier or an air conditioner, a medium (scaffold) for culturing a microorganism or biological tissue, a cosmetic article such as a sheet mask, and the like. The nonwoven fabric is also used for a liquid filter, a separation sheet for a battery, a membrane for a fuel cell, an extracorporeal inspection sheet such as a pregnancy test sheet, a medical sheet, a dustproof cloth for a dustproof mask and the like or a dustproof wear, a wiping sheet for wiping dust, and the like.

What is claimed is:

1. A nonwoven fabric containing a plurality of fibers having an average fiber diameter Dave in a range from 10 nm to 3 μm, inclusive, comprising:

a plurality of fusion portions among the plurality of fibers; and a first principal surface, and a second principal surface on an opposite side to the first principal surface, wherein an average number Nh of the fusion portions observed per 500 μm² on the first principal surface is six or more, wherein an average number Np of the fusion portions observed per 500 μm² off a cross-section perpendicular to the first principal surface of the nonwoven fabric satisfies Np>Nh.

2. The nonwoven fabric according to claim 1, wherein, in 70% or more of the fusion portions observed per 500 μm² on the first principal surface, a maximum length $L_{max}$ of the fusion portions and the average fiber diameter $D_{ave}$ satisfy $L_{max} \geq D_{ave}$.

3. The nonwoven fabric according to claim 1, wherein Np≥2 Nh is satisfied.

4. A dust collecting filter comprising:

a porous base layer;

a fiber layer laminated on the porous base layer; and a nonwoven fabric laminated on the porous base layer via the fiber layer, wherein the nonwoven fabric contains a plurality of fibers having an average fiber diameter $D_{ave}$ in a range from 500 nm to 3 μm, inclusive, and has a plurality of fusion portions among the plurality of fibers, a first principal surface, and a second principal surface on an opposite side to the first principal surface, wherein an average number Nh of the fusion portions observed per 500 μm² on the first principal surface is six or more, wherein an average number Np of the fusion portions observed per 500 μm² of a cross-section perpendicular to the first principal surface of the nonwoven fabric satisfies Np>Nh, and the fiber layer includes fibers having an average fiber diameter smaller than the average fiber diameter $D_{ave}$ of the fibers contained in the nonwoven fabric.

5. A medium for microorganisms or biological tissue, comprising a nonwoven fabric, wherein the nonwoven fabric contains a plurality of fibers having an average fiber diameter $D_{ave}$ in a range from 0.8 μm to 3 μm, inclusive, and has a plurality of fusion portions among the plurality of fibers, a first principal surface, and a second principal surface on an opposite side to the first principal surface, and an average number Nh of the fusion portions observed per 500 μm² on the first principal surface is six or more, wherein an average number Np of the fusion portions observed per 500 μm² of a cross-section perpendicular to the first principal surface of the nonwoven fabric satisfies Np>Nh.

6. A cosmetic article comprising a nonwoven fabric, wherein the nonwoven fabric contains a plurality of fibers having an average fiber diameter $D_{ave}$ in a range from 10 nm to 800 nm, inclusive, and has a plurality of fusion portions among the plurality of fibers, a first principal surface, and a second principal surface on an opposite side to the first principal surface, and an average number Nh of the fusion portions observed per 500 μm² on the first principal surface is six or more, wherein an average number Np of the fusion portions observed per 500 μm² of a cros-section perpendicular to the first principal surface of the nonwoven fabric satisfies Np>Nh.

* * * * *